United States Patent [19]

Monks et al.

[11] 4,038,033

[45] July 26, 1977

[54] SELENIUM LABELLED COMPOUNDS IN THE SATURATION ANALYSIS OF CYCLIC NUCLEOTIDE

[75] Inventors: Reginald Monks; Idris Lewis Thomas, both of Amersham, England

[73] Assignee: The Radiochemical Centre, Limited, England

[21] Appl. No.: 671,697

[22] Filed: Mar. 29, 1976

[30] Foreign Application Priority Data

Apr. 8, 1975 United Kingdom .............. 14462/75

[51] Int. Cl.$^2$ .................... C07H 19/10; C07H 19/20; G01N 33/16
[52] U.S. Cl. ................................. 23/230.3; 23/230.6; 424/1; 536/23; 536/24; 536/26; 536/27; 536/28; 536/29
[58] Field of Search ................ 23/230.3, 230.6, 230 B; 424/1, 1.5

[56] References Cited

U.S. PATENT DOCUMENTS 3,952,030   4/1976   Chambers et al. .................. 424/2 X

OTHER PUBLICATIONS

Albano et al., Factors Affecting the Saturation Assay of Cyclic AMP in Biological Systems, Chem. Abs., vol. 81, 47056k (1974).
Barling et al., Saturation Assay Method for Adenosine 3′,5′-Cyclic Monophosphate in Plasma and its Uses in Studies of the Action of Bovine Parathyroid Hormone, Chem. Abs., vol. 83, 72524k (1975).

*Primary Examiner*—Joseph Scovronek
*Attorney, Agent, or Firm*—Wenderoth, Lind & Ponack

[57] ABSTRACT

New selenium-75 labelled derivatives of cyclic nucleotides are described, which are of value in the saturation analysis of cyclic nucleotides, particularly adenosine-3′,5′-cyclic monophosphate (cyclic AMP) in body fluids.

1 Claim, No Drawings

SELENIUM LABELLED COMPOUNDS IN THE SATURATION ANALYSIS OF CYCLIC NUCLEOTIDE

This invention relates to methods of performing a saturation analysis of cyclic nucleotides characterised by the use of novel selenium-75 labelled cyclic nucleotides.

Certain cyclic nucleotides are implicated in the mechanism of hormonal control of bodily functions, and adenosine 3', 5'-cyclic monophosphate (Cyclic AMP) has been specficially referred to as the 'second messenger' in this control mechanism. Their measurements thus assume some importance, and information on cyclic nucleotide levels may assist in the diagnosis of certain disease states.

The measurement of cyclic nucleotides in body fluids may be effected by the methods of saturation analysis. These methods depend upon the competition between the cyclic nucleotide and its labelled version for binding sites on a specific protein, and a determination of the proportion of label bound after an appropriate separation procedure. Cyclic nucleotides labelled with tritium have been widely used in competitive protein binding assays. Although it would also be possible to use the phosphorus-32 labelled compounds in these assays, these suffer from the disadvantage of the short half-life of phosphorus-32 (14.3 days). Carbon-14 labelled compounds would have too low a specific radioactivity for use in these assays at the levels required.

Tritium, carbon-14 and phosphorus-32 are all $\beta$-emitting isotopes. Labelling with $\gamma$-emitters could provide more rapid and more economical counting although this would imply the use of foreign molecules. In the cyclic nucleotide field methods for the radioimmunoassay of adenosine 3', 5'-cyclic monophosphate (3', 5'-cyclic AMP) and guanosine 3', 5'-cyclic monophosphate (3', 5'-cyclic AMP) have utilised $\gamma$-emitting radioactive ligands prepared by coupling a $^{125}$I-iodinated tyrosine methyl ester to a 2'-O-hemisuccinyl cyclic nucleotide. We have found that selenium-75 is superior to iodine-125, for this purpose, in that it has a longer half-life (120 days) and a more energetic $\gamma$-emission which facilitates counting. Selenium-75 is also capable of stable incorporation into a number of positions in the cyclic nucleotide molecule.

By cyclic nucleotides, we mean compounds in which one of the following ribose cyclic phosphate groups is attached to one of the following bases.

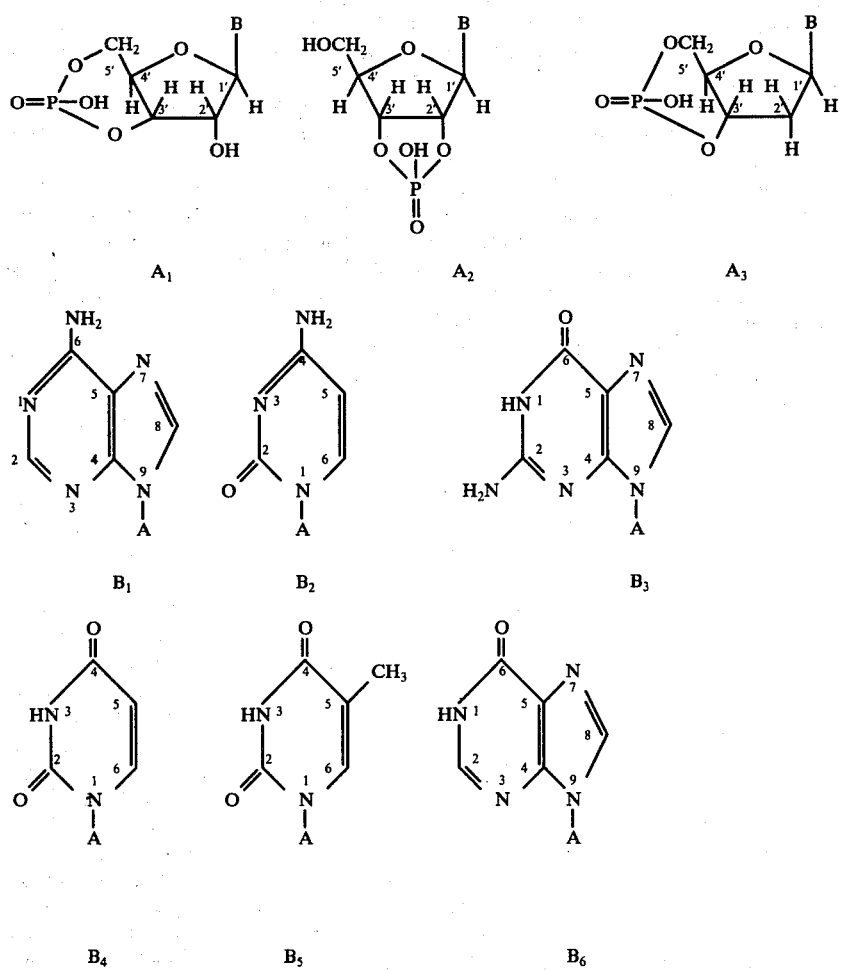

Some 8-substituted seleno derivatives of cyclic AMP have been described in the literature, e.g. 8-methyl-senoadenosine 3', 5'-cyclic monophosphate (J. Medicinal Chem. 17, 406, 1974); and 8-substituted selenoguanosine cyclic 3', 5'-phosphates (J. Medicinal Chem. 18, 559, 1975); no $^{75}$Se-labelled cyclic nucleotide derivatives have been reported. We herein describe the preparation of a range of cyclic nucleotide derivatives labelled with selenium-75 and have shown these materials to be of use as radioactive ligands in the saturation analysis of cyclic nucleotides. These $^{75}$Se-labelled derivatives fall into two classes: (i) those in which the purine or pyrimidine nucleus is substituted with groups containing selenium-75, and (ii) those in which a 2'-O-hemisuccinate of the cyclic nucleotide is coupled to an amine or amino-acid containing-selenium 75.

Products falling within the first class may be prepared by replacement of the halogen atom (usually chlorine or bromine) in halogen-substituted cyclic nucleotides, with hydrogen selenide ion HSe−. The selenol thus formed may be alkylated with an alkyl iodide to form an alkylseleno-derivative. The reactions may be carried out in an aqueous media. Other displacing nucleophiles, such as selenourea, may also be used. For example, 8-methylselenoadenosine 3', 5'cyclic monophosphate-$^{75}$Se, (I); 8-methylselenoguanosine 3',5'-cyclic monophosphate-$^{75}$Se, (II); and 6methylselenopurineriboside-3',5'-cyclic monophosphate-$^{75}$Se, (III) may be prepared respectively from the 8-bromo-cyclic AMP; 8-bromocyclic GMP; and 6-chloropurineriboside cyclic monophosphate. (I) and (III) have been shown to bind to a natural binding protein extracted from bovine muscle and to be capable of displacement with 3', 5'-cyclic AMP. (II) has been shown to bind to an antibody raised against cyclic GMP-2'-O-succinyl-BSA. They are, therefore, potentially useful as radioactive ligands in a competitive protein binding assay for 3', 5'-cyclic AMP.

Products falling within the second class may be prepared by reacting Se-methyl-L-selenocysteine[75]Se with 2'-O-hemisuccinate of a cyclic nucleotide in dimethylformamide in the presence of N-ethoxycarbonyl-2-ethoxy-dihydroquinoline (EEDQ). Such conjugates have been prepared from 3', 5'-cyclic AMP and 3', 5'-cyclic GMP and have been shown to bind strongly to antibodies raised against these cyclic nucleotides (IV and V).

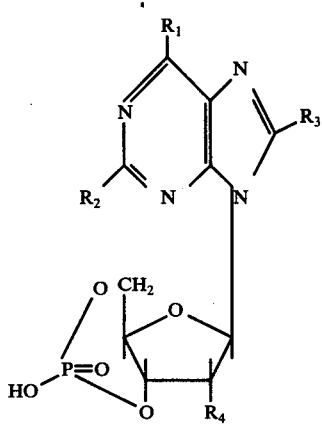

I. $R_1 = -NH_2$, $R_2 = -H$, $R_3$ 32 $SeCH_3$, $R_4 = -OH$
II. $R_1 = -OH$, $R_2 = -NH_2$; $R_3 = SeCH_3$, $R_4 = -OH$
III. $R_1 = -SeCH_3$, $R_2 = -H$, $R_3 = -H$, $R_4 = -OH$
IV. $R_1 = -NH_2$, $R_2 = -H$, $R_3 = -H$, $R_4 = -O-CO.CH_2CH_2CO.NHCH(COOH)CH_2SeCH_3$
V. $R_1 = -OH$, $R_2 = NH_2$, $R_3 = -H$, $R_4 = -O-CO.CH_2CH_2CO.NHCH(COOH)CH_2SeCH_3$.

The invention includes as new compounds selenium-75 labelled cyclic nucleotides in general, and particularly the following groups, of which No. i), ii), and iii) are the most important.

i. $A_1B_1$. Adenosine −3',5'-cyclic phosphate (cyclic AMP) substituted at the 6-, or 8-position, or at the 2' position for example:

8-methylseleno cyclic AMP, prepared from 8-bromocyclic AMP and sodium methylselenide;

6-methylselenopurine riboside cyclic phosphate, prepared from 6-chloropurine riboside cyclic phosphate and sodium methyl selenide;

N[6]-(2-methylselenoethyl) cyclic AMP, prepared from 6-chloropurineriboside cyclic phosphate and methylselenocysteamine.

ii. $A_1B_2$. Cystidine -3',5'-cyclic phosphate, substituted at the 2- or 4-position, or at the 2'-position.

iii. $A_1B_3$. Guanosine -3',5'-cyclic phosphate (cyclic GMP) substituted at the 2-, 6- or 8-position, or at the 2'-position, for example:

8-Methylseleno cyclic GMP, prepared from 8-bromo cyclic GMP and selenourea;

2-Methylseleno inosine -3', 5'-cyclic phosphate (cyclic IMP), prepared from 2-chloro cyclic IMP and sodium methylselenide;

2-Amino-6-methylselenopurine riboside cyclic phosphate, prepared from 2-amino-6-chloropurine riboside cyclic phosphate and sodium methyl selenide;

N[2]-(2-methylselenoethyl) cyclic GMP, prepared from 2-chloro cyclic IMP and methylselenocysteamine.

iv. $A_1B_4$. Uridine -3',5'-cyclic phosphate, substituted at the 2- or 4-position, or at the 2'-position.

v. $A_3B_5$. Thymidine -3',5'-cyclic phosphate, substituted at the 2- or 4-positions.

vi. $A_1B_6$. Inosine -3',5'-cyclic phosphate (cyclic IMP) substituted at the 2-, 6- or 8-position, or at the 2'-position.

In these examples, substituents on the purine or pyrimidine ring are either seleno- ($C_1$ to $C_4$) alkyl or N-($C_1$ to $C_4$) alkylseleno-($C_1$ to $C_4$) alkylamino groups; substituents on the ribose ring have the formula

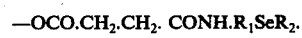

—OCO.CH$_2$.CH$_2$. CONH.R$_1$SeR$_2$.

where $R_1$ is a $C_1$ to $C_4$ alkylene groups which may carry a pendent —COOH group, and $R_2$ is a $C_1$ to $C_4$ alkyl group.

The selenium atoms include an artificially high proportion of Selenium-75.

The present invention also provides a method of performing a saturation analysis of a cyclic nucleotide by causing the nucleotide to be analysed and a radioactively labelled cyclic nucleotide to compete for reaction with a specific reagent for the said nucleotide, which is present in an amount insufficient to combine with all of said nucleotide and said labelled nucleotide, separating the bound nucleotide from the unbound nucleotide and measuring the radioactive concentration of one or both of the bound and the unbound nucleotide, characterised in that the radioactively labelled cyclic nucleotide is labelled with selenium-75.

The invention also provides an assay kit for performing the saturation analysis defined above, which kit comprises:

a. A specific reagent to combine with the cyclic nucleotide to be analysed;

b. a selenium-75 labelled cyclic nucleotide to compete with the cyclic nucleotide to be analysed for reaction with the specific reagent;

c. preferably, a supply of the cyclic nucleotide to be analysed, for use in preparing standards;

d. preferably, means for separating the bound nucleotide from the unbound nucleotide, and e. preferably, a plurality of tubes for performing the analysis.

EXAMPLE 1

Preparation of 8-methylseleno-adenosine-3',5'-cyclic monophosphate-$^{75}$Se

An aqueous solution of sodium selenide-$^{75}$Se was prepared by adding water (1ml) to a mixture of red selenium-$^{75}$Se (0.011 milliatom; 300mCi; 27Ci/mAtom) and sodium borohydride (1.6mg; 0.042mmol).

The mixture was stirred at room temperature under an atmosphere of nitrogen until all the selenium had dissolved. Excess sodium borohydride was destroyed by heating the solution at 100° C for 5 minutes. To the solution of sodium hydrogen selenide-$^{75}$Se was added 8-bromoadenosine-3',5'-cyclic monophosphate (5.2mg; 0.013mmol) in water (1ml) and the mixture was stirred and heated at 90°-95° C for 3½ hours.

The reaction mixture was treated with methyl iodide (0.5ml), dithiothreitol (5mg) and sodium carbonate (10mg) and was stirred at room temperature for 2 hours. It was then evaporated under reduced pressure to a small volume and the required product was isolated and purified by preparative thin-layer chromotography in two systems: system (1), 1mm silica gel (Merck 60 PF$_{254}$)/n-butanol, acetic acid, water (60:15:25); system (2), 1mm cellulose (Avicel)/n-butanol, acetic acid, water (60:15:25). The faster-running component of two UV absorbing radioactive bands in system (1) was rechromatographed in system (2). After autoradiography of the plate, the slower-running of the two components obtained in system (2) was extracted into water to yield 11mCi of 8-methylseleno-adenosine-3',5'-cyclic monophosphate-$^{75}$Se, $\lambda_{max}$287nm, $\epsilon$ max 16,300. Product identity was also confirmed by comparison with pure non-radioactive 8-methylseleno cyclic AMP in six chromatographic systems.

EXAMPLE 2

Preparation of 8-methylseleno-quanosine-3',5'-cyclic monophosphate-$^{75}$Se

An aqueous solution of sodium hydrogen selenide-$^{75}$Se was prepared by adding water(1ml) to a mixture of red selenium (0.016 milliatom; 421mCi; 26.2Ci/Atom) and sodium borohydride (1.5mg; 0.039mmol). The mixture was stirred at room temperature under nitrogen until all the selenium had dissolved. 5-methyl isothiouronium iodide (3.8mg; 0.017mmol) in water (0.5ml) was purged with nitrogen and added to the solution of sodium hydrogen selenide-$^{75}$Se. The reaction mixture was heated at ca. 90° C for 2 hours. The analysis of the reaction mixture after this time (PE1 cellulose/0.2 molar ammonium bicarbonate) showed a single radioactive component at Rf 0.60 in addition to red selenium-$^{75}$Se at Rf 0.00. The solution was lyophilized and the residue extracted with acetone (2ml). The acetone solution was evaporated to dryness to yield selenourea-$^{75}$Se (157mCi; 6.0 $\times$ 10$^{-3}$mmol), which was stored as the solid at $-140°$ C until needed.

8-bromoguanosine-3',5'-cyclic monophosphate (free acid; 3.2mg; 7.5 $\times$ 10$^{-3}$mmol) in anhydrous methanol (1ml) was added to the selenourea-$^{75}$Se (6.0 $\times$ 10$^{-3}$mmol) and the mixture was heated under reflux for 8 minutes and then allowed to cool. Sodium methoxide (1.2mg) in methanol (220$\mu$l) and methyl iodide (10$\mu$l) in methanol (250$\mu$l) were added in turn to the reaction mixture which was stirred at room temperature for 3 hours. The solution was evaporated to dryness and the residue purified by thin-layer chromatography using the system 1mm Avicel cellulose plate/94% aqueous butanol, 44% aqueous propionic acid (1;1). The main radioactive component, after location by autoradiography, was removed from the plate and extracted into water. The product (8.8mCi) was stored at $-140°$ C; it was shown to be 96% radiochemically pure but to contain a non-radioactive UV absorbing impurity. A portion of the product (0.3mCi) was applied to a DEAE Sephadex column (20 $\times$ 1cm) which was eluted with 0.1 molar ammonium bicarbonate. The main radioactive fraction, free from UV absorbing non-radioactive impurities, was collected and evaporated to dryness.

After evaporation with water to remove ammonium bicarbonate 8-methylselenoguanosine-3',5'-cyclic monophosphate-$^{75}$Se (0.22mCi) was obtained.

The product was shown to bind to an anti-body raised against cyclic GMP-2'-succinyl-BSA.

EXAMPLE 3

Coupling of 2'-O-succinyl-guanosine-3',5'-cyclic monophosphate to Se-methyl-L-selenocysteine-$^{75}$Se A solution of 2'-O-succinyl cyclic GMP (0.45mg; 1.0$\mu$mol) and N-ethoxycarbonyl-2-ethoxydihydroquinoline (0.7mg) in anhydrous dimethylformamide (75$\mu$l) was added to a solution of Se-methyl-L-selenocysteine-$^{75}$Se (16.1mCi; 1$\mu$mol) and triethylamine (5$\mu$l) in dimethylformamide (100$\mu$l). The reaction mixture was stirred overnight at room temperature. Thin-layer chromatography using the system Avicel cellulose/n-butanol, acetic acid, water (60:15:25) indicated the presence of two major radioactive components: Se-methyl-L-selenocysteine-$^{75}$Se at Rf 0.63 and the methylselenocysteine-$^{75}$Se conjugate of 2'-O-succinyl cyclic GMP at Rf 0.40. The condensation product (Rf 0.40) was isolated by preparative thin-layer chromatography, using 1mm Avicel cellulose and the above eluent system, to yield 0.7mCi of product.

EXAMPLE 4

Typical Dose Response Curve for an assay of cyclic AMP using 8-methylseleno-adenosine-3',5'-cyclic monophosphate-$^{75}$Se Standard solutions of cyclic AMP containing 1, 2, 4, 8 and 16 picomoles in 50mmol tris/4mmol EDTA buffer, pH 7.5 (50$\mu$l) were pipetted into assay tubes maintained at 2°-4° C. Buffer was also added to 'total' 'blank' and 'zero dose' tubes (150, 150 and 50$\mu$l respectively), also at 2-4° C. To each tube was added 8-methylseleno-cyclic AMP-$^{75}$Se (3 picomoles; specific activity ca 22Ci/mmol) in 50$\mu$l of buffer.

Binding protein (ex bovine muscle) in 100$\mu$l of buffer was then added to all tubes except the 'blanks'. The tubes were vortex mixed for approximately 5 seconds and then incubated at 2°-4° C for 3 hours. A suspension of charcoal in water (100$\mu$l) was added to all tubes except the 'totals' and after vortex mixing for approximately 5 seconds the tubes were immediately centrifuged to sediment the charcoal. A 200$\mu$l sample was removed from the supernate of each tube and from the totals and counted in a gamma counter.

Results are expressed in terms of $$\text{Percent bound} = \frac{\text{Counts - Blank count}}{\text{Total - Background}} \times 100$$

| Dose of cyclic AMP (Picomoles) | Percentage of $^{75}$Se-labelled cyclic AMP bound |
|---|---|
| 0 | 38.8 |
| 1 | 29.7 |
| 2 | 26.7 |
| 4 | 21.4 |
| 8 | 16.6 |
| 16 | 10.6 |

EXAMPLE 5

Typical Dose Response Curve for an assay of cyclic GMP using 8-methylseleno-guanosine-3',5'-cyclic monophosphate-$^{75}$Se Standard solutions of cyclic GMP containing 0.25, 0.5, 1.0, 2, 4, 8, and 16,000 picomoles in 100μl of 50mmol tris/4mmol EDTA buffer, pH 7.5, were pipetted into assay tubes maintained at 2°-4° C; the concentration of 16,000 picomoles/100μl was for determination of 'non-specific binding'. 100μl of buffer was also added to a tube for determination of 'zero dose' counts. To each tube was added 8-methylseleno-cyclic GMP-$^{75}$Se (0.25 picomoles, specific activity ca 24Ci/mmol) in 50μl of buffer. Antiserum (raised against cyclic GMP-2'-succinyl-BSA) in 50μl of buffer was then added to all tubes. The tubes were briefly vortex mixed and incubated at 2°-4° C for 3 hours. 1ml of aqueous ammonium sulphate solution (60% saturated) at 2°-4° C was added to all tubes which, after mixing, were kept at 2°-4° C for 5 minutes and then centrifuged. After decantation of the supernate and removal of adhering liquid the precipitates were counted in a gamma counter. 0.25 picomoles of 8-methylseleno-cyclic GMP-$^{75}$Se (specific activity ca 24Ci/mmol) in 50μl of buffer was also counted to give total counts.

Results are expressed in terms of $$\text{Percent bound} = \frac{\text{Counts bound - 'non-specific' counts}}{\text{Total - background}} \times 100$$

| Dose of cyclic GMP (picomoles) | Percentage of $^{75}$Se-labelled cyclic GMP bound |
|---|---|
| 0 | 45.3 |
| 0.25 | 33.7 |
| 0.5 | 27.8 |
| 1.0 | 22.3 |
| 2.0 | 14.0 |
| 4.0 | 9.3 |
| 8.0 | 6.5 |

EXAMPLE 6

Typical Dose Response Curve for an assay of cyclic GMP using the Se-methyl-L-selenocysteine-$^{75}$Se conjugate of 2'-O-succinyl cylic GMP Standard solutions of cyclic GMP containing 5, 10, 20, 40, 80 and 16,000 picomoles in 100μl of 50mmol tris/4mmol EDTA buffer, pH 7.5 were pipetted into assay tubes maintained at 2°-4° C; the concentration of 16,000 picomoles/100μl was for determination of 'non-specific binding'. 100μl of buffer was also added to a tube for determination of 'zero dose' counts. To each tube was added Se-methyl-L-selenocysteine-$^{75}$Se conjugate of 2'-O-succinyl cyclic GMP (0.59 picomoles; specific activity ca 16.1Ci/mmol of 50μl of buffer. Antiserum (raised against cyclic GMP-2'-succinyl-BSA) in 50μl of buffer was then added to all tubes. The tubes were briefly vortex mixed and incubated at 2°-4° C for 3 hours. 1ml of aqueous ammonium sulphate solution (60% saturated) at 2°-4° C was added to all tubes which, after mixing, were kept at 2°-4° C for 5 minutes and then centrifuged.

After decantation of the supernate and removal of adhering liquid the precipitates were counted in a gamma counter. 0.59 picomoles of the Se-methyl-L-selenocysteine-$^{75}$Se conjugate of 2'-O-succinyl cyclic GMP in 50μl of buffer was also counted to give total counts.

Results are expressed in terms of $$\text{Percent bound} = \frac{\text{Counts bound - 'non-specific' counts}}{\text{Total - Background}} \times 100$$

| Dose of cyclic GMP (picomoles) | Percentage of $^{75}$Se-labelled cyclic GMP bound |
|---|---|
| 0 | 24.5 |
| 5 | 17.3 |
| 10 | 16.7 |
| 20 | 11.8 |
| 40 | 8.3 |
| 80 | 6.1 |

EXAMPLE 7

Preparation of bis-6,6'-(purine riboside 3',5'-cyclic monophosphate)-diselenide-$^{75}$Se.

A solution of 6-chloropurine riboside 3',5'-cyclic monophosphate (5.0mg; 0.012mmol) and sodium hydrogen selenide-$^{75}$Se (0.06mmol) in water (2ml) was heated under nitrogen for 2 hours. The reaction mixture was applied to a DEAE Sephadex column (15 × 1cm) and eluted with 0.1 molar ammonium bicarbonate (500ml), 0.2 molar (500ml) and finally 0.3 molar (500ml). The main UV absorbing and radioactive fraction was collected and evaporated to dryness; repeated evaporation with water removed residual ammonium bicarbonate. The product of bis-6,6'-(purine riboside 3',5'-cyclic monophosphate)-diselenide-$^{75}$Se gave a UV spectrum having λmax 287nm. On reduction of the diselenide with dithiothreitol (10mg) in 1 molar tris buffer pH 7.5 (5ml) a change in the UV spectrum revealed the characteristic absorption of the 6-selenopurine at max 345nm.

Preparation of 6-methylselenopurine riboside 3',5'-cyclic monophosphate-$^{75}$Se Methyliodide (0.15ml) and dithiothreitol (12mg) were added to a solution of bis-6,6'-(purine riboside 3',5'-cyclic monophosphate)-diselenide-$^{75}$Se (3.7μmol; 40μCi) in 1 molar tris buffer pH 7.5 (5ml) and the mixture was stirred thoroughly for 1 hour. The solution was applied to a DEAE Sephadex column (15 × 2cm) which was then eluted with 0.2 molar ammonium bicarbonate. The main UV absorbing and radioactive fraction was collected and evaporated to dryness; repeated evaporation with water removed residual ammonium bicarbonate. Yield of 6-methylselenopurine riboside 3',5'-cyclic monophosphate-$^{75}$Se, 27μCi; λ max 231, 304nm (pH7). One component was revealed by chromatography with 0.2 molar ammonium bicarbonate on PEI cellulose.

EXAMPLE 8

Evaluation of 6-methylselenopurine riboside 3',5'-cyclic monophosphate-$^{75}$Se for use as a radioactive ligand in the saturation analysis of cyclic AMP Because of the low activity of the 6-methylselenopurine riboside 3',5'-cyclic monophosphate-$^{75}$Se its binding properties were investigated by using the selenuim-75 compound as a competitive inhibitor of the binding of tritiated cyclic AMP to the binding protein.

6-methylselenopurine riboside 3',5'-cyclic monophosphate-$^{75}$Se (specific activity 6.65mCi/mmol) was made up in tris/EDTA buffer at concentrations of 1,156 pmoles, 105pmoles and 9.6pmoles per 50μl aliquot. In the normal assay 100μl of binding protein is incubated with tritiated cyclic AMP (0.9pmol) and unlabelled cyclic AMP (standards and unknowns). Bound and free labelled cyclic AMP are separated by absorption of free cyclic AMP on charcoal and bound activity is determined by counting a sample of the supernate. To determine the potency of the selenium analogue the zero-dose binding was first determined, ie. the percentage of tritiated cylic AMP bound in the absence of unlabelled cyclic AMP or selenium analogue. This was then compared with the binding of tritiated cylic AMP in the presence of 4 different doses of selenium analogue. From the results obtained it was possible to calculate the amounts of unlabelled cyclic AMP which would give a reduction in binding equal to that caused by the selenium analogue.

The results in Table 1 show that 9.6pmoles of 6-methylselenopurine riboside 3',5'-cyclic monophosphate causes as much displacement of tritiated cyclic AMP as does 12.2 pmoles cyclic AMP, ie. at the concentration employed the two compounds have very similar binding powers.

Table 1

| Se analogue pmoles/50μl | % $^3$H-cyclic AMP bound | Cyclic AMP equivalent pmoles/50μl |
| --- | --- | --- |
| 0 | 54.5 | 0 |
| 1,156 | 0.42 | 161 |
| 105 | 0.96 | 69.7 |
| 9.6 | 5.06 | 12.2 |

We claim:

1. In a method of performing a saturation analysis of a cyclic nucleotide by providing a reaction mixture of the cyclic nucleotide to be analysed, a radioactively labelled cyclic nucleotide and a specific reagent for the said cyclic nucleotide, which specific reagent is present in an amount insufficient to combine with all of said cyclic nucleotide and said labelled cyclic nucleotide, effecting reaction of the reaction mixture, whereby part of the cyclic nucleotide becomes bound to the specific reagent and the remainder of the cyclic nucleotide does not become so bound, separating the cyclic nucleotide which is bound to said specific reagent from the cyclic nucleotide that is not so bound, and measuring the radioactive concentration of one or both of the bound and the unbound cyclic nucleotide, the improvement which consists in using as the radioactively labelled cyclic nucleotide, a cyclic nucleotide labelled with selenium-75.

* * * * *